United States Patent
Gong

(10) Patent No.: US 12,333,732 B2
(45) Date of Patent: Jun. 17, 2025

(54) SYSTEMS AND METHODS FOR IMAGE-BASED NERVE FIBER EXTRACTION

(71) Applicant: SHANGHAI UNITED IMAGING HEALTHCARE CO., LTD., Shanghai (CN)

(72) Inventor: Zhenhuan Gong, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 386 days.

(21) Appl. No.: 17/807,856

(22) Filed: Jun. 20, 2022

(65) Prior Publication Data
US 2022/0313384 A1    Oct. 6, 2022

Related U.S. Application Data

(63) Continuation of application No. PCT/CN2020/137836, filed on Dec. 20, 2020.

(30) Foreign Application Priority Data

Dec. 20, 2019 (CN) .................. 201911326191.X

(51) Int. Cl.
*G06T 7/00* (2017.01)
*A61B 90/00* (2016.01)
(Continued)

(52) U.S. Cl.
CPC ............... *G06T 7/11* (2017.01); *A61B 90/36* (2016.02); *G06V 10/25* (2022.01); *A61B 2090/364* (2016.02); *G06T 2207/10072* (2013.01)

(58) Field of Classification Search
CPC . G06T 7/11; G06T 2207/10072; A61B 90/36; A61B 2090/364; G06V 10/25
See application file for complete search history.

(56) References Cited

U.S. PATENT DOCUMENTS

| | | | |
|---|---|---|---|
| 2007/0124117 A1 | 5/2007 | Zhang | |
| 2010/0004527 A1* | 1/2010 | Dale | G01R 33/56341 |
| | | | 600/410 |

(Continued)

FOREIGN PATENT DOCUMENTS

| | | |
|---|---|---|
| CN | 103049901 A | 4/2013 |
| CN | 108734163 A | 11/2018 |

(Continued)

OTHER PUBLICATIONS

Eleftherios Garyfallidis et al., Dipy, a Library for the Analysis of Diffusion MRI Data, Frontiers in Neuroinformatics, 8(8): 1-17, 2014.

(Continued)

*Primary Examiner* — Khai M Nguyen
(74) *Attorney, Agent, or Firm* — METIS IP LLC

(57) ABSTRACT

The present disclosure provides methods and systems for image-based nerve fiber extraction. The methods may include obtaining an anatomical image of a subject and a diffusion image of the subject. The subject may include at least one region of interest (ROI) that relates to extraction of at least one target nerve fiber in the subject. The methods may further include determining, based on the anatomical image, the at least one ROI in the diffusion image; and extracting, from the diffusion image, at least one of the at least one target nerve fiber based on the at least one ROI.

19 Claims, 11 Drawing Sheets

(51) Int. Cl.
*G06T 7/11* (2017.01)
*G06V 10/25* (2022.01)

(56) References Cited

U.S. PATENT DOCUMENTS

| | | | |
|---|---|---|---|
| 2015/0293200 A1 | 10/2015 | Kurpad et al. | |
| 2017/0103525 A1* | 4/2017 | Hu | G06T 7/0012 |
| 2018/0005380 A1 | 1/2018 | Seiler et al. | |
| 2020/0005463 A1* | 1/2020 | Wu | G06T 7/149 |
| 2021/0353371 A1* | 11/2021 | Kou | A61B 90/37 |
| 2022/0317224 A1* | 10/2022 | Zuccolotto | G01R 33/58 |

FOREIGN PATENT DOCUMENTS

| | | | | |
|---|---|---|---|---|
| CN | 109741290 A | 5/2019 | | |
| CN | 109741346 A | 5/2019 | | |
| CN | 110415228 A | 11/2019 | | |
| EP | 2827167 A1 | 1/2015 | | |
| EP | 3407295 A1 | 11/2018 | | |
| WO | WO-2019070764 A1 * | 4/2019 | | A61B 5/0013 |
| WO | WO-2019135234 A1 * | 7/2019 | | A61B 34/20 |
| WO | 2021121415 A1 | 6/2021 | | |

OTHER PUBLICATIONS

Wang, Defeng et al., Tractography Atlas-based Spatial Statistics: Statistical Analysis of Diffusion Tensor Image along Fiber Pathways, Neuroimage, 2015, 10 pages.
Laura-Adela Harsan et al., In Vivo Diffusion Tensor Magnetic Resonance Imaging and Fiber Tracking of the Mouse Brain, NMR in Biomedicine, 23: 884-896, 2010.
The Extended European Search Report in European Application No. 20903966.8 mailed on Apr. 26, 2023, 11 pages.
International Search Report in PCT/CN2020/137836 mailed on Mar. 22, 2021, 5 pages.
Written Opinion in PCT/CN2020/137836 mailed on Mar. 22, 2021, 5 pages.
S. Wakana et al., Reproducibility of Quantitative Tractography Methods Applied to Cerebral White Matter, NeuroImage, 36: 630-644, 2007.
Yao, Xufeng et al., Research Progress of Fiber Bundle Tracking Algorithm in Magnetic Resonance Diffusion Tensor Imaging, Journal of Medical Research, 2012, 4 pages.
Ma, Kai et al., Nerve Fiber Tracking Methods Using Diffusion Tensor Imaging, Journal of Clinical Rehabilitative Tissue Engineering Research, 14(43): 7983-7986, 2010.
Wang, Defeng et al., Tractography Atlas-based Spatial Statistics: Statistical Analysis of Diffusion Tensor Image along Fiber Pathways, NeuroImage, 125: 301-310, 2015.

* cited by examiner

500

Obtaining an anatomical image of a subject and a diffusion image of the subject, the subject including at least one region of interest (ROI) that relates to extraction of at least one target nerve fiber in the subject ⟋⋀⟍ 502

Determining at least one ROI in the diffusion image based on the anatomical image ⟋⋀⟍ 504

Extracting at least one of the at least one target nerve fiber from the diffusion image based on the at least one ROI ⟋⋀⟍ 506

FIG. 5

SYSTEMS AND METHODS FOR IMAGE-BASED NERVE FIBER EXTRACTION

CROSS-REFERENCE TO RELATED APPLICATIONS

This application is a continuation of International Application No. PCT/CN2020/137836, filed on Dec. 20, 2020, which designates the United States of America and claims priority to Chinese Application No. 201911326191. X, filed on Dec. 20, 2019, the entire contents of which are hereby incorporated by reference.

TECHNICAL FIELD

The present disclosure generally relates to image processing, and more particularly, relates to systems and methods for image-based nerve fiber extraction.

BACKGROUND

Diffusion tensor imaging (DTI) is an advanced MRI (Magnetic Resonance Imaging, MRI) technology that can allow non-invasive observation of the macroscopic and microscopic anatomical structures of nerve fibers, such as brain white matter fibers. DTI utilizes the diffusion of water molecules to reveal microscopic details about tissue architecture.

Conventionally, when performing DTI imaging methods in the prior art, a DTI processing software is usually used to track the nerve fibers of the brain. The doctor manually draws or labels one or more regions of interest (ROIs) on the DTI image based on the anatomical data, and then one or more nerve fibers of interest are extracted based on the manually drawn ROI(s). However, such a conventional process of obtaining the ROI(s) of the DTI image by manual drawing is relatively cumbersome, which in turn leads to low efficiency of neural fiber tracking in the ROI. It is desired to develop more efficient systems and methods for determining the ROI(s) for extracting one or more nerve fibers of interest.

SUMMARY

According to an aspect of the present disclosure, a method for image-based nerve fiber extraction is provided. The method may be implemented on a computing device having at least one processor and at least one non-transitory storage medium. The method may include obtaining an anatomical image of a subject and a diffusion image of the subject, the subject including at least one region of interest (ROI) that relates to extraction of at least one target nerve fiber in the subject; determining, based on the anatomical image, the at least one ROI in the diffusion image; and extracting, from the diffusion image, at least one of the at least one target nerve fiber based on the at least one ROI.

In some embodiments, the determining, based on the anatomical image, the at least one ROI in the diffusion image may include determining, in the anatomical image, at least one reference region corresponding to the at least one ROI; and determining, based on the anatomical image and the at least one reference region, the at least one ROI in the diffusion image.

In some embodiments, the method of claim 2, wherein the determining, based on the anatomical image and the at least one reference region, the at least one ROI in the diffusion image may include determining registration information between the anatomical image and the diffusion image by registering the anatomical image with the diffusion image; and determining, in the diffusion image, the at least one ROI based on the registration information, the anatomical image, and the at least one reference region.

In some embodiments, the determining, in the anatomical image, at least one reference region corresponding to the at least one ROI may include obtaining at least one predetermined ROI mask; and determining, in the anatomical image, the at least one reference region based on the at least one predetermined ROI mask.

In some embodiments, the determining, in the anatomical image, at least one reference region corresponding to the at least one ROI may include obtaining a trained extraction model; and determining, in the anatomical image, at least one reference region using the trained extraction model.

In some embodiments, the trained extraction model is trained by a process including obtaining a preliminary extraction model; obtaining a plurality of training datasets, each of the plurality of training datasets including a historical anatomical image and at least one historical reference region identified in the historical anatomical image; and training the preliminary extraction model using the plurality of training datasets to obtain the trained extraction model.

In some embodiments, the determining, in the anatomical image, at least one reference region corresponding to the at least one ROI may include obtaining, based on at least one of a default setting or a user input, information related to the at least one target nerve fiber; and determining, based on the information related to the at least one target nerve fiber, the at least one reference region in the anatomical image.

In some embodiments, the extracting, from the diffusion image, at least one of the at least one target nerve fiber based on the at least one ROI may include identifying, based on the diffusion image, at least one candidate nerve fiber using a tracking algorithm; and extracting, from the diffusion image, the at least one of the at least one target nerve fiber selected from the at least one candidate nerve fiber.

In some embodiments, the identifying, based on the diffusion image, at least one candidate nerve fiber using a tracking algorithm may include determining a mask image by excluding one or more background regions from the diffusion image, the one or more background regions being unrelated to the extraction of the at least one target nerve fiber; and extracting, from the mask image, the at least one candidate nerve fiber using the tracking algorithm.

In some embodiments, the determining a mask image may include determining characteristic data based on the diffusion image; and determining the mask image based on the characteristic data.

In some embodiments, the determining a mask image may include obtaining the mask image by segmenting the diffusion image.

In some embodiments, the at least one ROI may include at least one of a first ROI or a second ROI. The at least one target nerve fiber may pass through the first ROI. The at least one target nerve fiber does not pass through the second ROI.

In some embodiments, the at least one ROI may include the first ROI, and the extracting, from the diffusion image, at least one of the at least one target nerve fiber based on the at least one ROI may include determining at least a portion of the first ROI as a seed point, and extracting, from the diffusion image and based on the seed point, the at least one of the at least one target nerve fiber that passes through the first ROI using a tracking algorithm.

In some embodiments, the at least one ROI may further include the second ROI, and the extracting, from the diffusion image and based on the diffusion image, the at least one of the at least one target nerve fiber that passes through the first ROI using a tracking algorithm may include determining, in the diffusion image and based on the seed point, at least one candidate nerve fiber that passes through the first ROI using the tracking algorithm; and for each of the at least one candidate nerve fiber, determining whether the candidate nerve fiber passes through the second ROI; and in response to determining that the candidate nerve fiber does not pass through the second ROI, designating the candidate nerve fiber as one of the at least one target nerve fiber.

In some embodiments, the method may further include obtaining a reference user input regarding the at least one ROI; and determining, based on the reference user input, whether to update at least a portion of the at least one ROI.

According to another aspect of the present disclosure, a system is provided. The system may include at least one non-transitory storage medium including a set of instructions for image-based nerve fiber extraction and at least one processor in communication with the at least one non-transitory storage medium. When executing the set of instructions, the at least one processor is configured to cause the system to perform operations including obtaining an anatomical image of a subject and a diffusion image of the subject, the subject including at least one region of interest (ROI) that relates to extraction of at least one target nerve fiber in the subject; determining, based on the anatomical image, the at least one ROI in the diffusion image; and extracting, from the diffusion image, at least one of the at least one target nerve fiber based on the at least one ROI.

According to yet another aspect of the present disclosure, a non-transitory computer readable medium is provided. The non-transitory computer readable medium may include at least one set of instructions. When executed by at least one processor of a computing device, the at least one set of instructions may direct the at least one processor to perform operations including obtaining an anatomical image of a subject and a diffusion image of the subject, the subject including at least one region of interest (ROI) that relates to extraction of at least one target nerve fiber in the subject; determining, based on the anatomical image, the at least one ROI in the diffusion image; and extracting, from the diffusion image, at least one of the at least one target nerve fiber based on the at least one ROI.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein:

FIG. 5 is a flowchart illustrating an exemplary process for target nerve fiber extraction according to some embodiments of the present disclosure;

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, section or assembly of different level in ascending order. However, the terms may be displaced by another expression if they achieve the same purpose. The term "image" in the present disclosure is used to collectively refer to image data (e.g., scan data, projection data) and/or images of various forms, including a two-dimensional (2D) image, a three-dimensional (3D) image, a four-dimensional (4D), etc.

Figure 2:
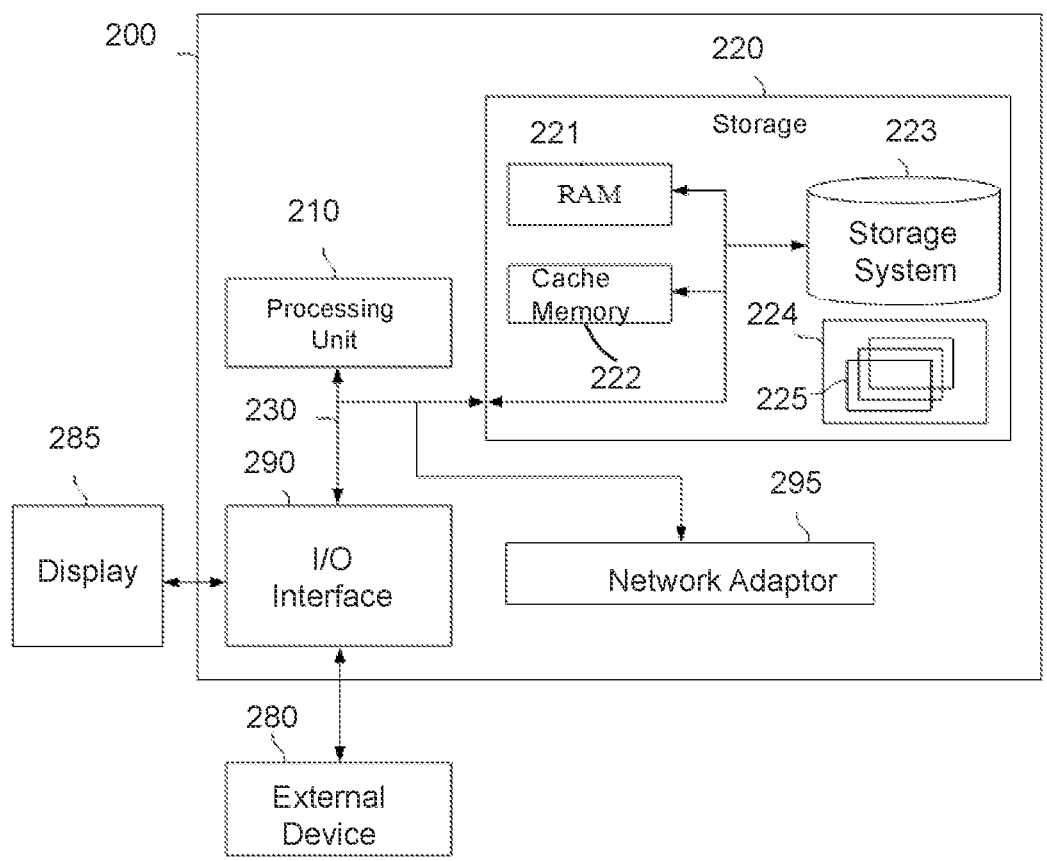
FIG. 2 is a schematic diagram illustrating an exemplary nerve fiber extraction device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 210 as illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

Figure 1:
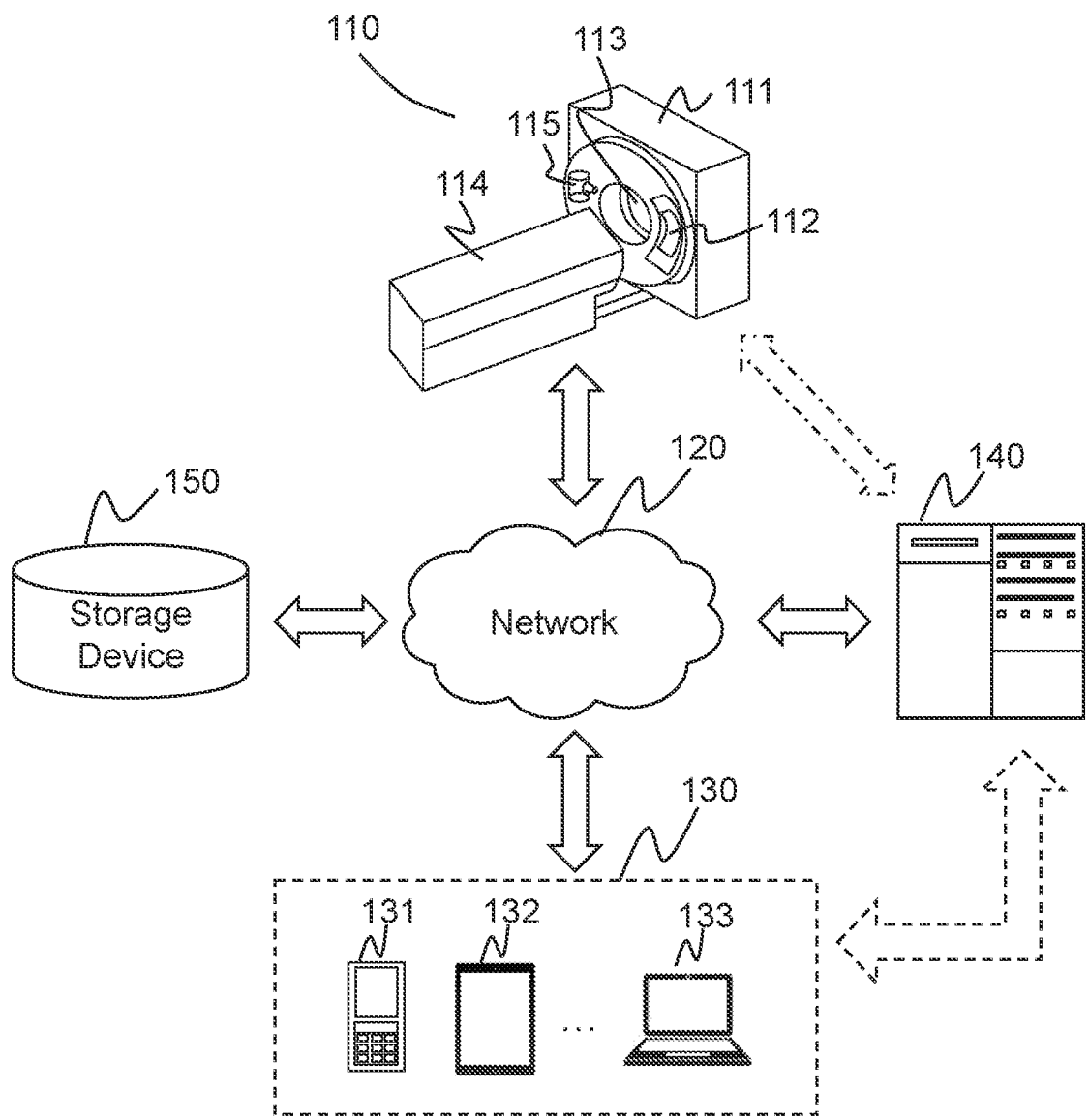
FIG. 1 is a schematic diagram illustrating an exemplary imaging system according to some embodiments of the present disclosure.

FIG. 1 is a schematic diagram illustrating an exemplary system 100 for image-based nerve fiber extraction according to some embodiments of the present disclosure. As shown, the system 100 may include an imaging device 110, a network 120, one or more terminals 130, a processing device 140, and a storage device 150. In some embodiments, the imaging device 110, the terminal(s) 130, the processing device 140, and/or the storage device 150 may be connected to and/or communicate with each other via a wireless connection (e.g., the network 120), a wired connection, or a combination thereof. The connection between the components of the system 100 may be variable. Merely by way of example, the imaging device 110 may be connected to the processing device 140 through the network 120, as illustrated in FIG. 1. As another example, the imaging device 110 may be connected to the processing device 140 directly. As a further example, the storage device 150 may be connected to the processing device 140 through the network 120, as illustrated in FIG. 1, or connected to the processing device 140 directly. As still a further example, a terminal 130 may be connected to the processing device 140 through the network 120, as illustrated in FIG. 1, or connected to the processing device 140 directly.

The imaging device 110 may generate or provide image data via scanning a subject (e.g., a patient) disposed on a scanning table of the imaging device 110. In some embodiments, the imaging device 110 may include a single-modality scanner and/or multi-modality scanner. The single-modality scanner may include, for example, a computed tomography (CT) scanner, a magnetic resonance imaging (MRI) scanner, an ultrasonography scanner, a positron emission tomography (PET) scanner, etc. The multi-modality scanner may include a single photon emission computed tomography-computed tomography (SPECT-CT) scanner, a positron emission tomography-computed tomography (PET-CT) scanner, a computed tomography-ultra-sonic (CT-US) scanner, a digital subtraction angiography-computed tomography (DSA-CT) scanner, or the like, or a combination thereof. In some embodiments, the image data may include projection data, images relating to the subject, etc. The projection data may be raw data generated by the imaging device 110 by scanning the subject or data generated by a forward projection on an image relating to the subject. In some embodiments, the subject may include a body, a substance, an object, or the like, or a combination thereof. In some embodiments, the subject may include a specific portion of a body, such as a head, a thorax, an abdomen, or the like, or a combination thereof. In some embodiments, the subject may include a specific organ or region of interest, such as an esophagus, a trachea, a bronchus, a stomach, a gallbladder, a small intestine, a colon, a bladder, a ureter, a uterus, a fallopian tube, etc.

In some embodiments, the imaging device 110 may include a gantry 111, a detector 112, a detecting region 113, a scanning table 114, and a radioactive scanning source 115. The gantry 111 may support the detector 112 and the radioactive scanning source 115. A subject may be placed on the scanning table 114 to be scanned. The radioactive scanning source 115 may emit radioactive rays to the subject. The radiation may include a particle ray, a photon ray, or the like, or a combination thereof. In some embodiments, the radiation may include a plurality of radiation particles (e.g., neutrons, protons, electrons, p-mesons, heavy ions), a plurality of radiation photons (e.g., X-ray, a y-ray, ultraviolet, laser), or the like, or a combination thereof. The detector 112 may detect radiations and/or radiation events (e.g., gamma photons) emitted from the detecting region 113. In some embodiments, the detector 112 may include a plurality of detector units. The detector units may include a scintillation detector (e.g., a cesium iodide detector) or a gas detector. The detector unit may be a single-row detector or a multi-rows detector.

In some embodiments, the imaging device 110 may be integrated with one or more other devices that may facilitate the scanning of the subject, such as an image-recording device. The image-recording device may be configured to take various types of images related to the subject. For example, the image-recording device may be a two-dimensional (2D) camera that takes pictures of the exterior or outline of the subject. As another example, the image-recording device may be a 3D scanner (e.g., a laser scanner, an infrared scanner, a 3D CMOS sensor) that records the spatial representation of the subject.

The network 120 may include any suitable network that can facilitate exchange of information and/or data for the system 100. In some embodiments, one or more components of the system 100 (e.g., the imaging device 110, the processing device 140, the storage device 150, the terminal(s) 130) may communicate information and/or data with one or more other components of the system 100 via the network 120. For example, the processing device 140 may obtain image data from the imaging device 110 via the network 120. As another example, the processing device 140 may obtain user instruction(s) from the terminal(s) 130 via the network 120. The network 120 may be or include a public network (e.g., the Internet), a private network (e.g., a local area network (LAN)), a wired network, a wireless network (e.g., an 802.11 network, a Wi-Fi network), a frame relay network, a virtual private network (VPN), a satellite network, a telephone network, routers, hubs, switches, server computers, and/or any combination thereof. For example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired and/or wireless network access points such as base stations and/or internet exchange points through which one or more components of the system 100 may be connected to the network 120 to exchange data and/or information.

The terminal(s) 130 may be connected to and/or communicate with the imaging device 110, the processing device 140, and/or the storage device 150. For example, the terminal(s) 130 may obtain a processed image from the processing device 140. As another example, the terminal(s) 130 may obtain image data acquired via the imaging device 110 and transmit the image data to the processing device 140 to be processed. In some embodiments, the terminal(s) 130 may include a mobile device 131, a tablet computer 132, a laptop computer 133, or the like, or any combination thereof. For example, the mobile device 131 may include a mobile phone, a personal digital assistant (PDA), a gaming device, a navigation device, a point of sale (POS) device, a laptop, a tablet computer, a desktop, or the like, or any combination thereof. In some embodiments, the terminal(s) 130 may include an input device, an output device, etc. The input device may include alphanumeric and other keys that may be input via a keyboard, a touch screen (for example, with haptics or tactile feedback), a speech input, an eye tracking input, a brain monitoring system, or any other comparable input mechanism. The input information received through the input device may be transmitted to the processing device 140 via, for example, a bus, for further processing. Other types of the input device may include a cursor control device, such as a mouse, a trackball, or cursor direction keys, etc. The output device may include a display, a speaker, a printer, or the like, or a combination thereof. In some embodiments, the terminal(s) 130 may be part of the processing device 140.

The processing device 140 may process data and/or information obtained from the imaging device 110, the storage device 150, the terminal(s) 130, or other components of the system 100. For example, the processing device 140 may reconstruct an image based on scan data generated by the imaging device 110. As another example, the processing device 140 may be directed to extract one or more target nerve fibers from a diffusion image. As yet another example, the processing device 140 may be directed to determine at least one ROI in the diffusion image that is related to the extraction of the one or more target nerve fibers. In some embodiments, the processing device 140 may be a single server or a server group. The server group may be centralized or distributed. In some embodiments, the processing device 140 may be local to or remote from the system 100. For example, the processing device 140 may access information and/or data from the imaging device 110, the storage device 150, and/or the terminal(s) 130 via the network 120. As another example, the processing device 140 may be directly connected to the imaging device 110, the terminal(s) 130, and/or the storage device 150 to access information and/or data. In some embodiments, the processing device 140 may be implemented on a cloud platform. For example, the cloud platform may include a private cloud, a public cloud, a hybrid cloud, a community cloud, a distributed cloud, an inter-cloud, a multi-cloud, or the like, or a combination thereof. In some embodiments, the processing device 140 may be implemented by a computing device 200 having one or more components as described in connection with FIG. 2.

The storage device 150 may store data, instructions, and/or any other information. In some embodiments, the storage device 150 may store data obtained from the processing device 140, the terminal(s) 130, and/or the storage device 150. In some embodiments, the storage device 150 may store data and/or instructions that the processing device 140 may execute or use to perform exemplary methods described in the present disclosure. In some embodiments, the storage device 150 may include a mass storage device, a removable storage device, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage device 150 may be implemented on a cloud platform as described elsewhere in the disclosure.

In some embodiments, the storage device 150 may be connected to the network 120 to communicate with one or more other components of the system 100 (e.g., the processing device 140, the terminal(s) 130). One or more components of the system 100 may access the data or instructions stored in the storage device 150 via the network 120. In some embodiments, the storage device 150 may be part of the processing device 140.

This description is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. For example, the storage device 150 may be a data storage including cloud computing platforms, such as public cloud, private cloud, community, and hybrid clouds, etc. However, those variations and modifications do not depart the scope of the present disclosure.

FIG. 2 is a schematic diagram illustrating an exemplary nerve fiber extraction device according to some embodiments of the present disclosure. The nerve fiber extraction device 200 shown in FIG. 2 is provided for illustration purposes, and should not bring any limitation to the function and application scope of the embodiments of the present disclosure.

As shown in FIG. 2, the nerve fiber extraction device 200 is represented in the form of a computing device. The components of the nerve fiber extraction device 200 in the ROI may include, but are not limited to: one or more processors or processing units 210, a storage 220, and a bus 230 connecting different system components (including the storage 220 and the processing unit 210).

The bus 230 represents one or more of several types of bus structures, including a memory bus, a memory controller, a peripheral bus, a graphics acceleration port, a processor, or a local bus using any bus structure among multiple bus structures. For example, these architectures include but are not limited to industry standard architecture (ISA) bus, microchannel architecture (MAC) bus, enhanced ISA bus, Video Electronics Standards Association (VESA) local bus, and peripheral component interconnection (PCI) bus.

The nerve fiber extraction device 200 of the ROI typically includes a variety of computer system readable media. These media may be any available media that can be accessed by the nerve fiber extraction device 200, including volatile and nonvolatile media, removable and non-removable media.

The storage 220 may include computer system readable media in the form of volatile memory, such as random access memory (RAM) 221 and/or cache memory 222. The nerve fiber extraction device 200 of the ROI may further include other removable/non-removable, volatile/nonvolatile computer system storage media. For example only, the storage system 223 can be used to read and write non-removable, non-volatile magnetic media (not shown in FIG. 8, usually referred to as a "hard drive"). Although not shown in FIG. 8, a disk drive for reading and writing to removable/non-volatile disks (such as "floppy disks"), as well as removable non-volatile disks (such as CD-ROM, DVD-ROM or other optical media) read and write optical disc drives. In these cases, each drive can be connected to the bus 230 through one or more data media interfaces. The memory 220 may include at least one program product having a set of program modules 225(for example, the obtaining module 410, the extracting module 420 and the tracking module 430 of the nerve fiber extraction device 400), which are configured to execute a nerve fiber extraction process described in the present disclosure.

In some embodiments, a program/utility tool 224 including the set of program modules 225 can be stored in the memory 220. For example, such program modules 225 may include but not limited to an operating system, one or more application programs, other program modules, program data, etc. Each of these examples or a certain combination may include the implementation of a network environment. The program module 225 generally executes the functions and/or methods in the described embodiments of the present disclosure.

The nerve fiber extraction device 200 can also communicate with one or more external devices 280 (such as keyboards, pointing devices, a display 285, etc.), and can also communicate with one or more devices that allow user interactions (e.g., a terminal device). The extraction device 200 may also communicate with one or more devices (such as a network card, modem, etc.) that enables the nerve fiber extraction device 200 to communicate with one or more other computing devices. Such communication can be performed through an input/output (I/O) interface 290. In addition, the nerve fiber extraction device 200 may also communicate with one or more networks (for example, a local area network (LAN), a wide area network (WAN), and/or a public network, such as the Internet) through a network adapter 295. As shown in the figure, the network adapter 295 may communicate with other components of the nerve fiber extraction device 200 through the bus 230. It should be understood that although not shown in the figure, other hardware and/or software modules can be used in conjunction with the nerve fiber extraction device 200, including but not limited to: microcomputers, device drivers, redundant processing units, external disk drive arrays, RAID systems, tape drives, and data backup storage systems, etc.

The processing unit 210 may implement various functions by running programs stored in the storage 220, such as implementing a method for extracting nerve fibers related to at least one ROI provided by some embodiments of the present disclosure. The method may include obtaining an anatomical image and a diffusion image (e.g., a diffusion tensor image) of a current detection part, where the diffusion image includes the diffusion data of the current detection part, and the anatomical image contains the anatomical data of the current detection part; extracting at least one ROI of the diffusion image based on the anatomical data, the diffusion data, and the pre-stored ROI mask data of the current detection part; and tracking a target nerve fiber in the diffusion image using a preset tracking algorithm based on the at least one ROI.

The processing unit 210 may execute various functions by running programs stored in the storage 220, such as implementing a method for extracting nerve fibers based on at least one ROI provided by some embodiments of the present disclosure.

Figure 3:
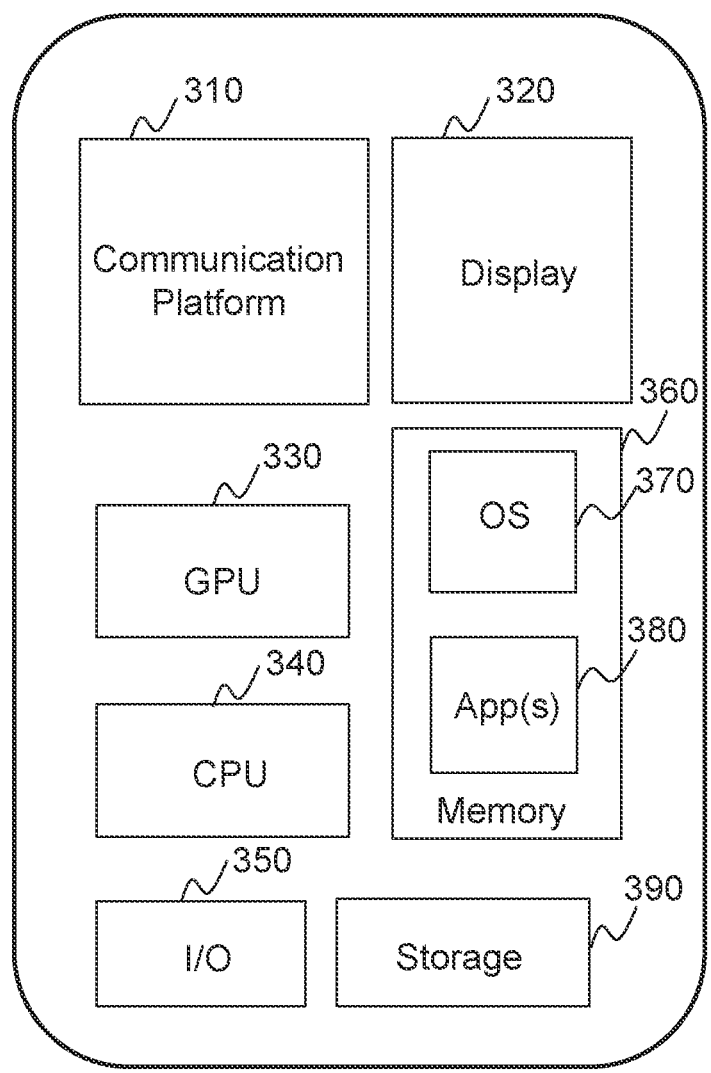
FIG. 3 is a schematic diagram illustrating exemplary hardware and/or software components of an exemplary mobile device according to some embodiments of the present disclosure.

FIG. 3 is a schematic diagram illustrating exemplary hardware and/or software components of an exemplary mobile device 300 on which the terminals 130 may be implemented according to some embodiments of the present disclosure. As illustrated in FIG. 3, the mobile device 300 may include a communication platform 310, a display 320, a graphic processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS™, Android™, Windows Phone™) and one or more applications 380 may be loaded into the memory 360 from the storage 390 in order to be executed by the CPU 340. The applications 380 may include a browser or any other suitable mobile apps for receiving and rendering information relating to image processing or other information from the processing device 140. User interactions with the information stream may be achieved via the I/O 350 and provided to the processing device 140 and/or other components of the system 100 via the network 120.

To implement various modules, units, and their functionalities described in the present disclosure, computer hardware platforms may be used as the hardware platform(s) for one or more of the elements described herein. A computer with user interface elements may be used to implement a personal computer (PC) or any other type of work station or terminal device. A computer may also act as a server if appropriately programmed.

Figure 4:
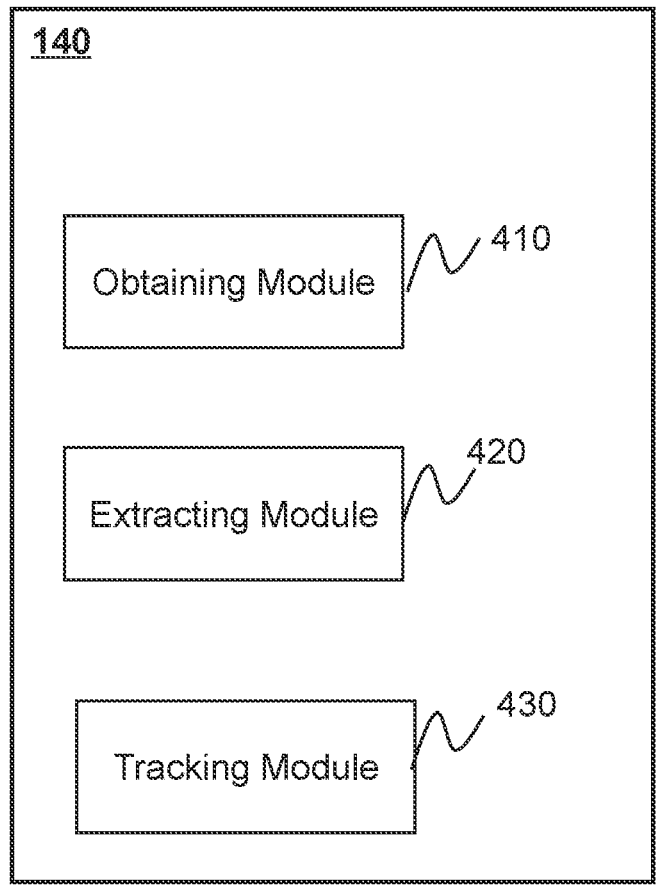
FIG. 4 is a block diagram illustrating an exemplary nerve fiber extraction device according to some embodiments of the present disclosure.

FIG. 4 is a block diagram illustrating an exemplary nerve fiber extraction device 400 according to some embodiments of the present disclosure. In some embodiments, the nerve fiber extraction device 400 may be implemented on a processing device (e.g., the processing device 140). As illustrated in FIG. 4, the nerve fiber extraction device 400 may include an obtaining module 410, an extracting module 420, and a tracking module 430. The modules may be hardware circuits of all or part of the nerve fiber extraction device 400. The modules may also be implemented as an application or set of instructions read and executed by the nerve fiber extraction device 400. Further, the modules may be any combination of the hardware circuits and the application/instructions. For example, the modules may be the part of the nerve fiber extraction device 400 when the nerve fiber extraction device 400 is executing the application/set of instructions.

The obtaining module 410 may acquire data related to the system 100. For instance, the obtaining module 410 may obtain an anatomical image of a subject and a diffusion image of the subject. The subject may include at least one region of interest (ROI) that relates to extraction of at least one target nerve fiber in the subject. For example, the subject may include a specific portion of a patient, such as the head, the abdomen, the spine, the heart, or the like, or a combination thereof, of a patient. In some embodiments, the at least one ROI may include an ROI through which a target nerve fiber passes. As used herein, an ROI through which a target nerve fiber passes is also referred to as a first ROI. Additionally or alternatively, the at least one ROI may include an ROI though which no target nerve fiber pass. As used herein, an ROI through which no target nerve fiber passes is also referred to as a second ROI; that is a second ROI is void of a target nerve fiber.

The extracting module 420 may extract at least one ROI in the diffusion image based on the anatomical image and other data obtained by the obtaining module 410. In some embodiments, the processing device 140 may determine at least one reference region corresponding to the at least one ROI in the anatomical image. For example, the processing device 140 may determine the at least one reference region in the anatomical image using a trained extraction model or a predetermined template (also referred to as an "ROI mask"). The trained extraction model and the predetermined ROI mask may correspond to the at least one target nerve fiber to be extracted. For instance, the processing device 140 may retrieve the trained extraction model or the predetermined ROI mask from the storage device according to the information related to the at least one target nerve fiber.

The tracking module 430 may track at least one target nerve fibers based on the at least one ROI determined by the extracting module 420. For instance, the at least one ROI may include a first ROI and a second ROI. The tracking module 430 may track all the nerve fibers in the diffusion image using a tracking algorithm, and designate all the tracked nerve fibers as the candidate nerve fibers. The tracking module 430 may further select at least one candidate nerve fiber that passes through the first ROI but does not pass through the second ROI as at least one target nerve fiber. Alternatively, the tracking module 430 may determine at least one candidate nerve fiber that passes through the first ROI based on a regional growth method using the seed point. For each of the at least one candidate nerve fiber, the tracking module 430 may determine whether the candidate nerve fiber passes through the second ROI; and in response to determining that the candidate nerve fiber does not pass through the second ROI, the tracking module 430 may designate the candidate nerve fiber as one of the at least one target nerve fiber. For instance, the seed point may be determined based on a first ROI through which a target nerve fiber may pass. The seed point may include a point in the first ROI, a region in the first ROI, the entire first ROI, etc. More details regarding the determination of the at least one candidate nerve fiber may be found elsewhere in the present disclosure, for example, in FIG. 9, FIG. 10, and the description thereof.

It should be noted that the above description is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure. In some embodiments, any module mentioned above may be divided into two or more units. In some embodiments, the nerve fiber extraction device 400 may include one or more additional modules. For example, the nerve fiber extraction device 400 may further include a control module configured to generate control signals for one or more components in the system 100. In some embodiments, one or more modules of the nerve fiber extraction device 400 described above may be omitted.

FIG. 5 is a flowchart illustrating an exemplary process for target nerve fiber extraction according to some embodiments of the present disclosure. At least a portion of process 500 may be implemented on the nerve fiber extraction device 200 as illustrated in FIG. 2 or the nerve fiber extraction device 400 as illustrated in FIG. 4. In some embodiments, one or more operations of the process 500 may be implemented in the system 100 as illustrated in FIG. 1. In some embodiments, one or more operations in the process 500 may be stored in the storage device 150 and/or the storage (e.g., the storage 220, etc.) as a form of instructions, and invoked and/or executed by the system 100, or a portion thereof (e.g., the processing device 140). In some embodiments, the instructions may be transmitted in a form of electronic current or electrical signals.

In 502, the processing device 140 (e.g., the obtaining module 410) may obtain an anatomical image of a subject and a diffusion image of the subject. The subject may include at least one region of interest (ROI) that relates to extraction of at least one target nerve fiber in the subject. For example, the subject may include a specific portion of a patient, such as the head, the abdomen, the spine, the heart, or the like, or a combination thereof, of a patient. Merely by way of example, the subject may include the brain, and the at least one target nerve fiber may include a corticospinal tract, an optic tract, an upper longitudinal tract, a lower longitudinal tract, a cingulate, a corpus callosum, or the like, or any combination thereof.

In some embodiments, the at least one ROI may include an ROI through which a target nerve fiber passes. As used herein, an ROI through which a target nerve fiber passes is also referred to as a first ROI. Additionally or alternatively, the at least one ROI may include an ROI though which no target nerve fiber pass. As used herein, an ROI through which no target nerve fiber passes is also referred to as a second ROI; that is a second ROI is void of a target nerve fiber. For example, the at least one ROI may include one or more first ROIs, and a target nerve fiber to be extracted may pass through each of the one or more first ROIs. As another example, the at least one ROI may include one or more second ROIs, a target nerve fiber to be extracted does not pass through any of the one or more second ROIs. As yet another example, a target nerve fiber may pass through one or more first ROIs but not any second ROI. Additionally or alternatively, the at least one ROI may include a selection group of ROIs. A target nerve fiber may pass through at least some (e.g., one) of the selection group of ROIs.

As used herein, the term "anatomical image" refers to an image showing an anatomical structure of the subject, and/or information thereof. In some embodiments, the anatomical image may be acquired using a medical imaging device (e.g., the imaging device 110) by a scan of the subject. The imaging device may include a CT device, an X-ray imaging device, an MRI device, a PET device, an ultrasound imaging device, a DR device, etc.

As used herein, the term "diffusion image" refers to an image acquired using a diffusion-weighted magnetic resonance imaging technique. The diffusion-weighted magnetic resonance imaging technique utilizes the diffusion of water molecules to generate contrast in an MR image. Water molecule diffusion patterns can reveal microscopic details about tissue architecture. Merely by way of example, the diffusion-weighted magnetic resonance imaging technique may include a diffusion tensor imaging (DTI) technique, which is commonly used in image-based extraction of one or more nerve fibers in the brain. More details regarding the DTI technique may be found elsewhere in the present disclosure. See, for example, the description of operation 602. In some embodiments, the anatomical image and the diffusion image obtained in operation 502 may relate to a same portion of a patient, such as the head of the patient. Merely by way of example, the anatomical image may be a normal MR image of the subject, and the diffusion image may be a diffusion tensor image of the subject. As yet another example, the diffusion image may be acquired using a diffusion kurtosis imaging (DKI) technique that extends conventional DTI by estimating the kurtosis of the water diffusion probability distribution function.

In 504, the processing device 140 (e.g., the extracting module 420) may determine at least one ROI in the diffusion image based on the anatomical image. In some embodiments, the at least one ROI includes one or more first ROIs through which at least one target fiber passes. Additionally or alternatively, the at least one ROI may include one or more second ROIs through which no target fiber pass.

In some embodiments, the processing device 140 may obtain information related to the at least one target nerve fiber. For example, the information related to the at least one target nerve fiber may include a name, a classification, a length, a diameter, or the like, or any combination thereof, of the at least one target nerve fiber. Such information may be obtained from a default setting stored in a storage device (e.g., the storage device 150). Alternatively, a user may input at least some of the information related to the at least one target nerve fiber via a terminal device. For example, the user may input the name(s) of the at least one target fiber through an input device (e.g., a keyboard) of the terminal device. As another example, the terminal device may display names of a plurality of nerve fibers. The user may specify the at least one target nerve fiber by selecting at least one of the plurality of nerve fibers via the input device (e.g., a keyboard and/or a mouse).

In some embodiments, the processing device 140 may determine at least one reference region corresponding to the at least one ROI in the anatomical image. For example, the processing device 140 may determine the at least one reference region in the anatomical image using a trained extraction model or a predetermined template (also referred to as an "ROI mask"). The trained extraction model and the predetermined ROI mask may correspond to the at least one target nerve fiber to be extracted. For instance, the processing device 140 may retrieve the trained extraction model or the predetermined ROI mask from the storage device according to the information related to the at least one target nerve fiber.

The processing device 140 may further determine the at least one ROI in the diffusion image based on the at least one reference region and registration information between the anatomical image and the diffusion image.

To obtain the registration information between the anatomical image and the diffusion image, the processing device 140 may register the anatomical image and the diffusion image using an image registration algorithm. For example, the image registration algorithm may include an intensity-based algorithm, a feature-based algorithm, a coordinate transformation algorithm, a spatial domain algorithm, a frequency domain algorithm, or the like, or any combination thereof. The registration information may include, for example, a registration matrix, a mapping relationship between pixels (or voxels) of the anatomical image and pixels (or voxels) of the diffusion image. More details regarding the registration of the anatomical image and the diffusion image may be found elsewhere in the present disclosure, for example, in FIGS. 6 and 7.

In some embodiments, the processing device 140 may transmit information of the at least one ROI (or referred to as ROI information) to a terminal device for display. Merely by way of example, the ROI information may be in the form of an image, e.g., a portion of the diffusion image that includes primarily the at least one ROI. As used herein, "primarily" indicates that at least a certain percentage (e.g., at least 50%, at least 60%, at least 70%, at least 80%, at least 90%, at least 95%) of the portion includes or is occupied by a representation of the at least one ROI. The ROI information may include a representation of the at least one ROI indicating at least one feature of the at least one ROI including, e.g., the shape, the position, the size, or the like, or a combination thereof, of each of the at least one ROI. A user may view the ROI information on a display of the terminal device and check whether the ROI information needs to be updated. The processing device 140 may obtain a reference user input regarding the ROI information, and determines whether to update at least a portion of one or more of the at least one ROI. If the user decides that at least a portion of the ROI information needs to be updated, the user may, for example, adjust the shape, the position, and/or the size of any one of the at least one ROI. If the user decides that none of the ROI information needs to be updated, the user may input an instruction to the terminal device to cause the processing device 140 proceed to operation 506.

In 506, the processing device 140 (e.g., the tracking module 430) may extract at least one of the at least one target nerve fiber from the diffusion image based on the at least one ROI. In some embodiments, the processing device 140 may determine a mask image in the diffusion image and extract the at least one of the at least one target nerve fiber from the mask image. As used herein, the mask image determined in the diffusion image refers to a portion of the diffusion image that excludes one or more background regions that are unrelated to the extraction of the at least one target nerve fiber. For instance, the one or more background regions may include a region where nerve fibers in the subject (or the at least one target nerve fiber) are unlikely to pass, or the like, or any combination thereof. More descriptions regarding the mask image and the ROI extraction from the mask image may be found elsewhere in the present disclosure, for example, in FIG. 9 and the description thereof.

In some embodiments, the processing device 140 may select one or more target nerve fibers from at least one candidate nerve fiber based on the at least one ROI. For instance, the at least one ROI may include a first ROI and a second ROI. The processing device 140 may track all the nerve fibers in the diffusion image using a tracking algorithm, and designate all the tracked nerve fibers as the candidate nerve fibers. The processing device 140 may further select at least one candidate nerve fiber that passes through the first ROI but does not pass through the second ROI as at least one target nerve fiber. Alternatively, the processing device 140 may determine at least one candidate nerve fiber that passes through the first ROI based on a regional growth method using the seed point. For each of the at least one candidate nerve fiber, the processing device 140 may determine whether the candidate nerve fiber passes through the second ROI; and in response to determining that the candidate nerve fiber does not pass through the second ROI, the processing device 140 may designate the candidate nerve fiber as one of the at least one target nerve fiber. For instance, the seed point may be determined based on a first ROI through which a target nerve fiber may pass. The seed point may include a point in the first ROI, a region in the first ROI, the entire first ROI, etc. More details regarding the determination of the at least one candidate nerve fiber may be found elsewhere in the present disclosure, for example, in FIG. 9, FIG. 10, and the description thereof.

It should be noted that the above description regarding the process 500 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure.

Figure 6:
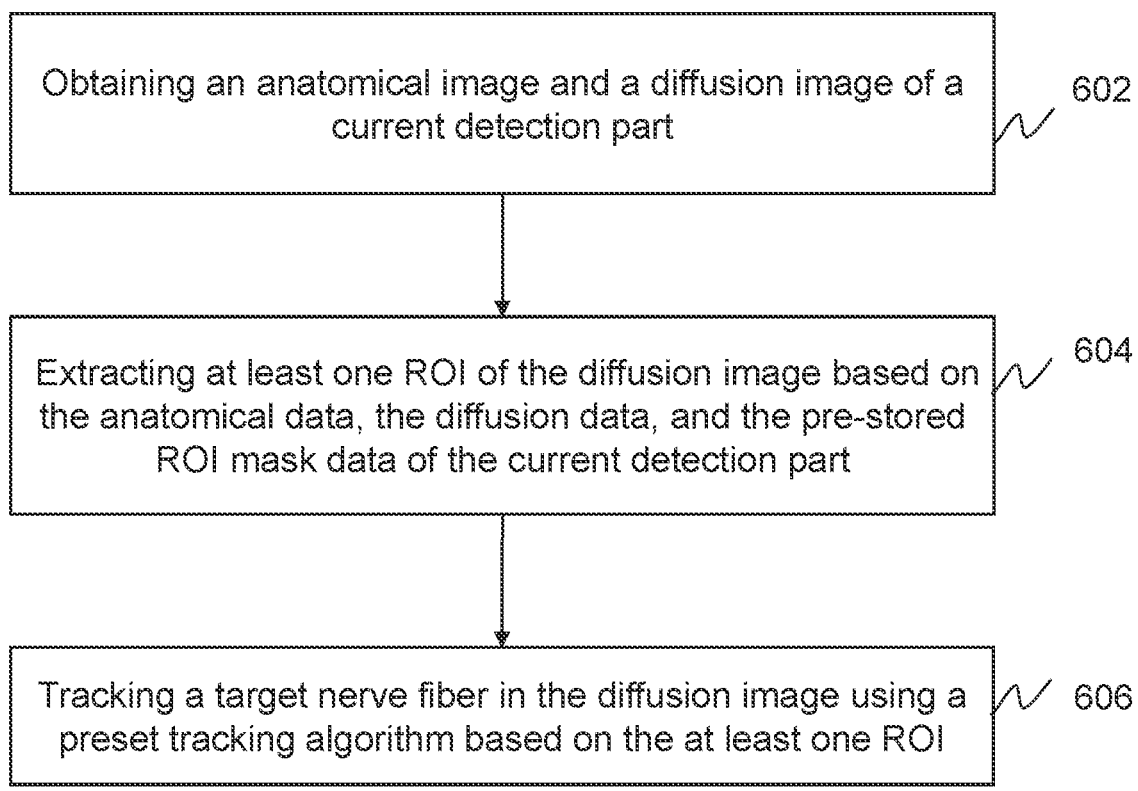
FIG. 6 is a flowchart illustrating an exemplary process for extracting nerve fibers related to at least one ROI according to some embodiments of the present disclosure.

FIG. 6 is a flowchart illustrating an exemplary process for extracting nerve fibers related to at least one ROI according to some embodiments of the present disclosure. Process 600 is suitable for automatically extracting at least one ROI and performing nerve fiber tracking based on the automatically extracted ROI. At least a portion of process 600 may be implemented on the nerve fiber extraction device 200 as illustrated in FIG. 2 or the nerve fiber extraction device 400 as illustrated in FIG. 4. In some embodiments, one or more operations of the process 600 may be implemented in the system 100 as illustrated in FIG. 1. In some embodiments, one or more operations in the process 600 may be stored in the storage device 150 and/or the storage (e.g., the storage 220, etc.) as a form of instructions, and invoked and/or executed by the system 100, or a portion thereof (e.g., the processing device 140). In some embodiments, the instructions may be transmitted in a form of electronic current or electrical signals).

In 602, an anatomical image and a diffusion image of a current detection part may be obtained. In some embodiments, operation 602 may be performed by the processing device 140, for example, the extracting module 420.

The current detection part, also referred to as a subject, may include, for example, the head, the chest, etc., of a patient. The subject may also be referred to as a current detection part. For illustration purposes and not intended to limiting the scope of the present disclosure, the following description is provided with reference to the head of a patient as the current detection part.

The diffusion image may include, for example, a DWI image, a DTI image, a DKI image, or the like. The diffusion tensor image is a kind of magnetic resonance image obtained by using the diffusion tensor imaging technology. The diffusion tensor image may utilize the difference in diffusion characteristics of water molecules in the brain tissue structure to obtain an image of the brain. Therefore, the diffusion tensor image can present the distribution of nerve fibers through the diffusion of water molecules. It should be noted that the process 600, 700, 800, 900, 1000, and 1100 may also be implemented to extract at least one target nerve fiber from various forms of diffusion images, such as a DWI image or a DTI image.

The diffusion image includes diffusion data of the current detection part. The anatomical image includes anatomical data of the current detection part.

In some embodiments, the diffusion image may include multiple sets of diffusion data each in the form of a matrix. For example, the diffusion data may include a DWI image $B_0$ without any gradient, a first gradient-applied DWI image $D_1$, and a second gradient-applied DWI image $D_2, \ldots$, and an $n^{th}$ gradient-applied DWI image $D_n$, where n is an integer. For instance, n is an integer no less than 6.

In 604, at least one ROI of the diffusion image may be extracted based on the anatomical data, the diffusion data, and the pre-stored ROI mask data (also referred to as the "predetermined ROI mask" or "predetermined ROI mask data") of the current detection part. In some embodiments, operation 604 may be performed by the extracting module 420.

The ROI mask data of the current detection part may be standard mask data related to the current detection part. For instance, a user may obtain a historical anatomical image of the current detection part of a sample patient. The sample patient may be the current patient or a different patient. The user may manually determine one or more ROIs in the historical anatomical image to generate the ROI mask data.

In some embodiments, a mapping relationship or a mapping matrix among the anatomical data, the diffusion data, and the ROI mask data can be established to obtain a relationship between the diffusion data and the ROI mask data. At least one ROI of the diffusion image may be further determined based on the relationship and the ROI mask data.

In some embodiments, if the automatically extracted ROI does not meet the needs of the user, the processing device 140 may obtain one or more editing instructions for the ROI of the diffusion image from the user. The ROI of the diffusion image may be updated according to the editing instructions to obtain re-extracted ROI of the diffusion tensor until the re-extracted ROI meets the requirements.

In 606, a target nerve fiber in the diffusion image may be tracked using a preset tracking algorithm based on the at least one ROI. In some embodiments, operation 606 may be performed by the tracking module 430.

In some embodiments, the preset tracking algorithm may include at least one of the Fiber Assignment Continuous Tracking (FACT) algorithm or the TensorLine algorithm. For instance, according to the FACT algorithm for tracking the nerve fibers of interest (also referred to as the target nerve fibers), the tracking may start from the center point of a seed voxel (or pixel), extend along a main feature direction of the diffusion tensor until an adjacent pixel or voxel is reached, then change the tracking direction into the main diffusion direction of the newly increased speed, and proceed according to this process until a pixel or voxel satisfying an end condition is reached. Therefore, after at least one ROI of the diffusion image is extracted, a pixel or voxel may be selected for each of the at least one ROI as a seed point. A growth operation may start from each seed point, combined with the diffusion characteristics of water molecules in the brain tissue, until the growth of each nerve fiber of interest is completed. In this way, at least one target nerve fiber in the at least one ROI can be determined.

In some embodiments, the target nerve fibers may include at least one of the corticospinal tract, the optic tract, the upper longitudinal tract, the lower longitudinal tract, the cingulate, the corpus callosum, or the like, or any combination thereof.

By automating the process of target nerve fiber extraction may improve the tracking efficiency and/or accuracy, reduce cross-user variations, compared to manual extraction according to conventional methods.

It should be noted that the above description regarding the process 600 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure.

Figure 7:
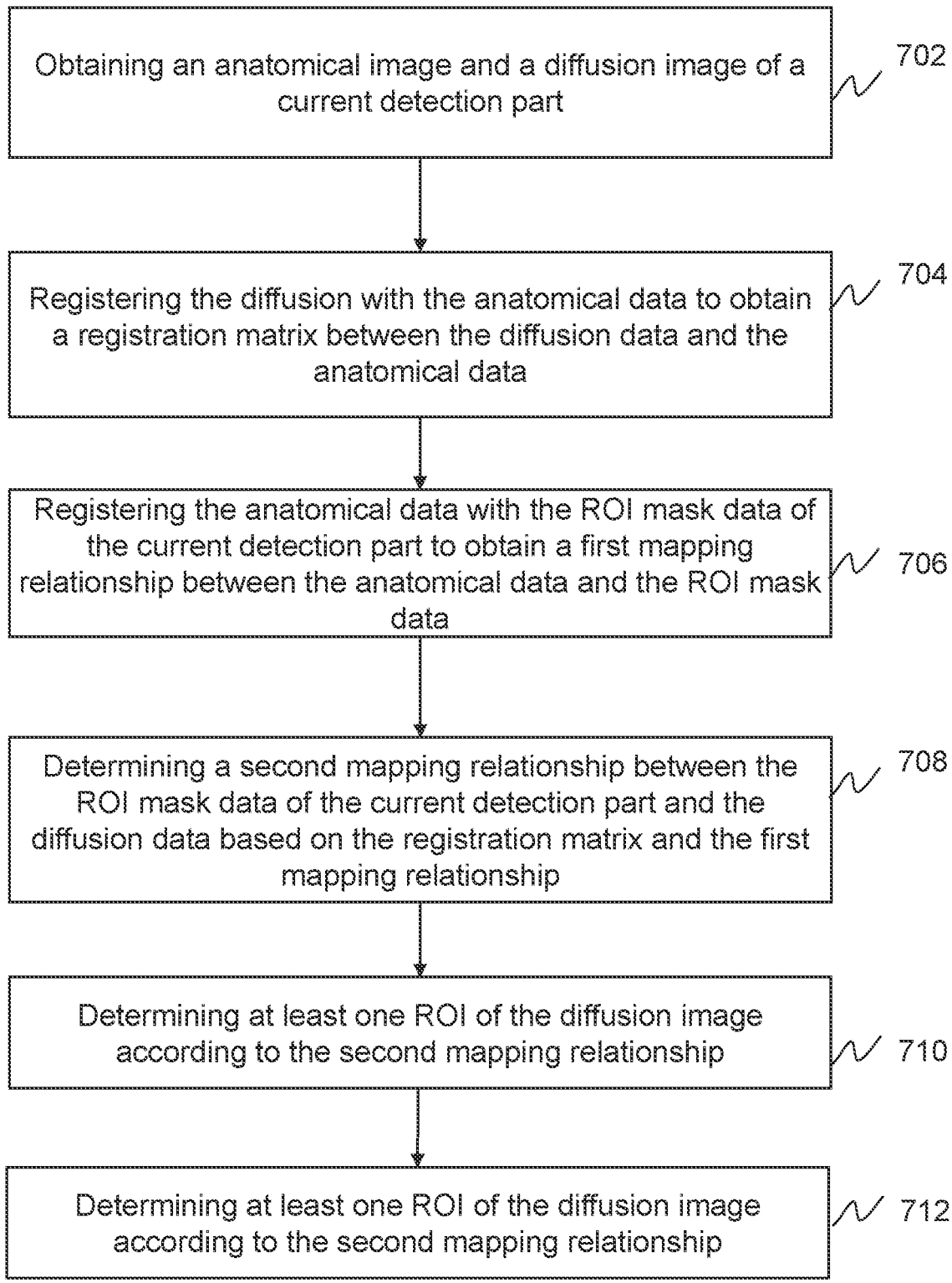
FIG. 7 is a flowchart of illustrating an exemplary process for extracting at least one target nerve fiber.

FIG. 7 is a flowchart illustrating an exemplary process for extracting at least one target nerve fiber. At least a portion of process 700 may be implemented on the nerve fiber extraction device 200 as illustrated in FIG. 2 or the nerve fiber extraction device 400 as illustrated in FIG. 4. In some embodiments, one or more operations of the process 700 may be implemented in the system 100 as illustrated in FIG. 1. In some embodiments, one or more operations in the process 700 may be stored in the storage device 150 and/or the storage (e.g., the storage 220, etc.) as a form of instructions, and invoked and/or executed by the system 100, or a portion thereof (e.g., the processing device 140). In some embodiments, the instructions may be transmitted in a form of electronic current or electrical signals.

In 702, an anatomical image and a diffusion image of a current detection part may be obtained.

In 704, the diffusion data may be registered with the anatomical data to obtain a registration matrix between the diffusion data and the anatomical data.

Optionally, the registration of the diffusion data and the anatomical data may be rigid registration or non-rigid registration. For example, the B0 data of the diffusion data may be registered with the anatomical data. Alternatively, the Di ($1<=i<=n$) data of the diffusion data may be registered with the anatomical data. The diffusion data used for the registration is not specifically limited by the present disclosure.

In 706, the anatomical data may be registered with the ROI mask data of the current detection part to obtain a first mapping relationship between the anatomical data and the ROI mask data.

Optionally, the registration of the diffusion data and the ROI mask data of the current detection part may be rigid registration or non-rigid registration.

In 708, a second mapping relationship between the ROI mask data of the current detection part and the diffusion data may be determined based on the registration matrix and the first mapping relationship.

It is understandable that the registration matrix may include the corresponding relationship between the diffusion data and the anatomical data. The first mapping relationship may include the corresponding relationship between the anatomical data and the ROI mask data of the current detection part. Therefore, the second mapping relationship between the ROI mask data and the diffusion data of the current detection position can be obtained based on the matrix and the first mapping relationship, that is, the corresponding relationship between the ROI mask data and the diffusion data can be obtained.

In 710, at least one ROI of the diffusion image may be determined according to the second mapping relationship. In some embodiments, operations 704-710 may be performed by the extracting module 420.

It is understandable that since the second mapping relationship includes the corresponding relationship between the ROI mask data of the current detection position and the diffusion data, at least one ROI of the diffusion image can be automatically determined according to the second mapping relationship.

In 712, a preset tracking algorithm may be used to track at least one target nerve fiber based on the at least one ROI.

It should be noted that the above description regarding the process 600 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure.

Figure 8:
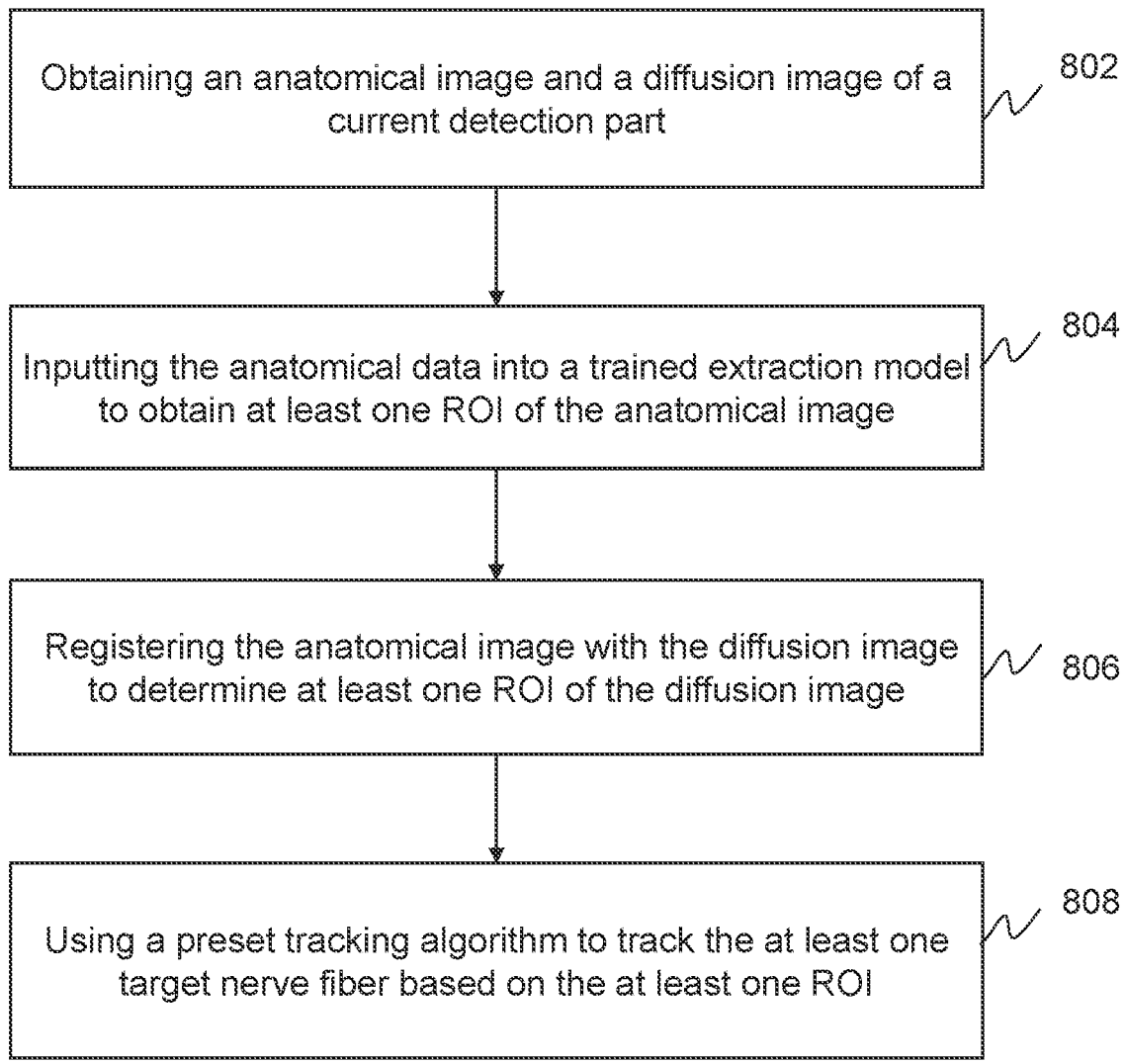
FIG. 8 is a flowchart illustrating an exemplary process for extracting at least one target nerve fiber according to some embodiments of the present disclosure.

FIG. 8 is a flowchart illustrating an exemplary process for extracting at least one target nerve fiber according to some embodiments of the present disclosure. At least a portion of process 800 may be implemented on the nerve fiber extraction device 200 as illustrated in FIG. 2 or the nerve fiber extraction device 400 as illustrated in FIG. 4. In some embodiments, one or more operations of the process 800 may be implemented in the system 100 as illustrated in FIG. 1. In some embodiments, one or more operations in the process 800 may be stored in the storage device 150 and/or the storage (e.g., the storage 220, etc.) as a form of instructions, and invoked and/or executed by the system 100, or a portion thereof (e.g., the processing device 140). In some embodiments, the instructions may be transmitted in a form of electronic current or electrical signals.

In 802, an anatomical image and a diffusion image of a current detection part may be obtained.

In 804, the anatomical data may be inputted into a trained extraction model to obtain at least one ROI of the anatomical image.

The trained extraction model is obtained by training a preliminary extraction model (e.g., a neural network model) using a plurality of training datasets. Each of the plurality of training datasets may include a historical anatomical image and at least one historical reference region identified in the historical anatomical image. It is understandable that the historical reference region may be identified manually in the historical anatomical image.

Optionally, the preliminary extraction model may be a deep learning network model or a convolutional neural network model, or the like, which is not limited by the present disclosure.

In 806, the anatomical image may be registered with the diffusion image to determine at least one ROI of the diffusion image.

Optionally, the registration of the at least one ROI of the anatomical image and the diffusion image may be rigid registration or non-rigid registration.

In 808, a preset tracking algorithm may be used to track the at least one target nerve fiber based on the at least one ROI.

Optionally, the original neural network can be trained using at least one area of interest of the standard diffusion image and the standard diffusion image to obtain the trained extraction model, and then input the acquired diffusion image of the current detection part After the training is completed, at least one ROI of the diffusion image can be obtained.

It should be noted that the above description regarding the process 800 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure.

Figure 9:
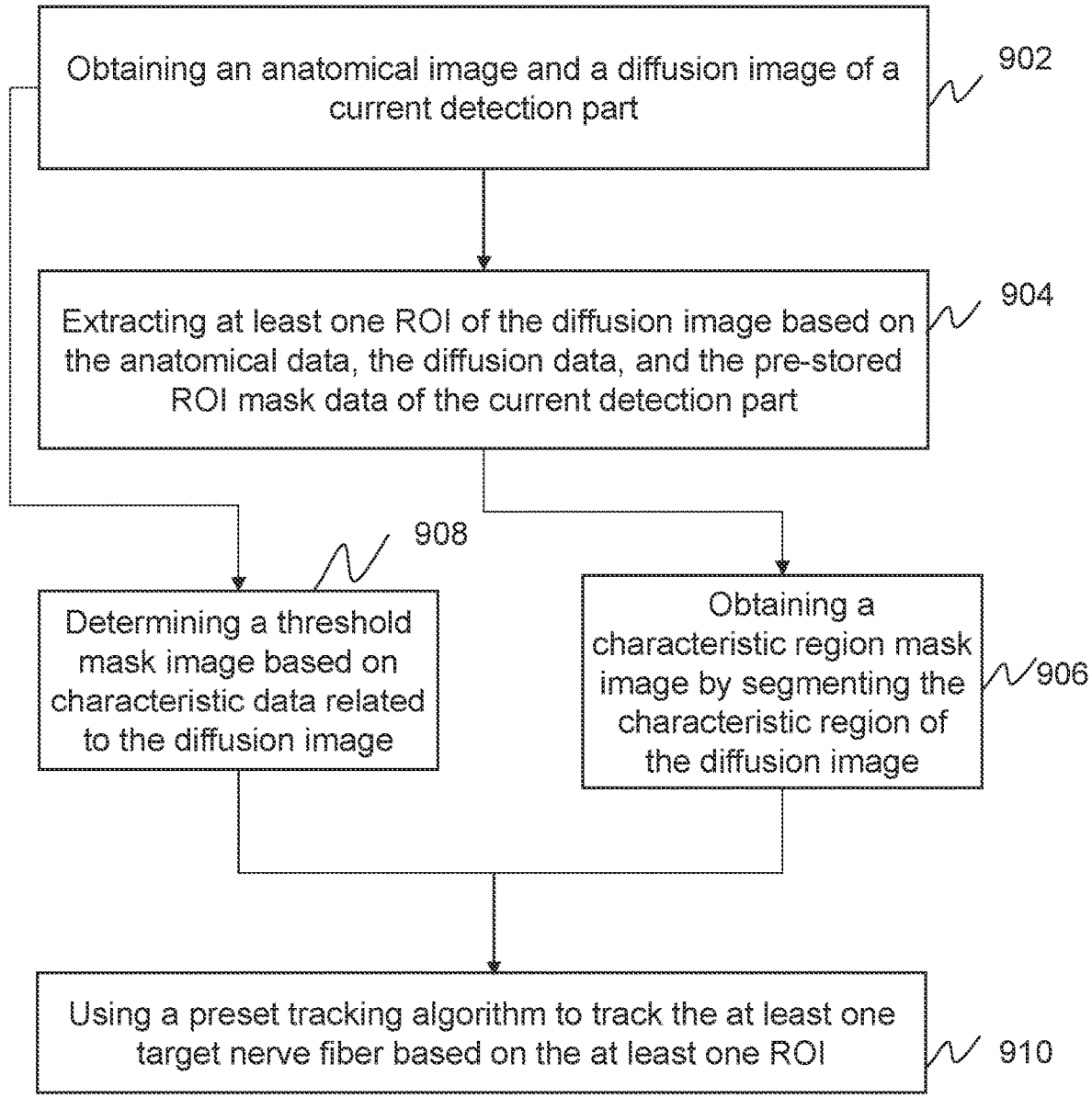
FIG. 9 is a flowchart illustrating an exemplary process for extracting at least one target nerve fiber according to some embodiments of the present disclosure.

FIG. 9 is a flowchart illustrating an exemplary process for extracting at least one target nerve fiber according to some embodiments of the present disclosure. At least a portion of process 900 may be implemented on the nerve fiber extraction device 200 as illustrated in FIG. 2 or the nerve fiber extraction device 400 as illustrated in FIG. 4. In some embodiments, one or more operations of the process 900 may be implemented in the system 100 as illustrated in FIG. 1. In some embodiments, one or more operations in the process 900 may be stored in the storage device 150 and/or the storage (e.g., the storage 220, etc.) as a form of instructions, and invoked and/or executed by the system 100, or a portion thereof (e.g., the processing device 140). In some embodiments, the instructions may be transmitted in a form of electronic current or electrical signals.

In 902, an anatomical image and a diffusion image of a current detection part may be obtained.

In 904, at least one ROI of the diffusion image may be extracted based on the anatomical data, the diffusion data, and the pre-stored ROI mask data of the current detection part. In some embodiments, the processing device 140 may proceed to operation 906 or 908 to determine a mask image, and then proceed to operation 910 to track the at least one target nerve fiber in the mask image. The mask image may include, for example, a characteristic region mask image or a threshold mask image.

In 906, the characteristic region mask image may be obtained by segmenting the characteristic region of the diffusion image.

In some embodiments, the characteristic region may include the brain, the chest, etc. Optionally, if the characteristic region is the brain, the segmentation of the characteristic region of the diffusion image may be implemented by removing a region corresponding to the scalp from the diffusion image, thereby obtaining a brain mask image.

In 908, the threshold mask image may be determined based on characteristic data related to the diffusion image. The characteristic data may be determined based on the diffusion data.

Merely by way of example, the diffusion image may be a DTI image, and the diffusion data may include the trace of the diffusion tensor and other data. For example, Trace=$\lambda 1 + \lambda 2 + \lambda 3$, where $\lambda 1$, $\lambda 2$, and $\lambda 3$ are the three characteristic directions of the diffusion data, respectively. The characteristic data may include partial anisotropy index FA, Volume Ratio (VR), relative anisotropy index RA, etc., where FA, VR and RA are all calculated from $\lambda 1$, $\lambda 2$, and $\lambda 3$. Therefore, After the feature data is obtained, the threshold of the feature data can be adjusted to determine the threshold mask image of the diffusion tensor data.

In 910, a preset tracking algorithm may be used to track the at least one target nerve fiber based on the at least one ROI.

Optionally, the at least one target nerve fiber in the characteristic region mask image or the threshold mask image can be tracked according to a preset tracking algorithm to obtain at least one candidate nerve fiber. For instance, the at least one ROI may include at least one first ROI that the at least one target nerve fiber passes through. The processing device 140 may designate one or more candidate nerve fibers that pass through the at least one first ROI as the target nerve fiber.

It is understandable that the above method may be implemented in a processing device. The user can control the tracking of the at least one target nerve fiber in the diffusion image by importing configuration files and/or inputting instructions to the nerve fiber extraction device of the ROI (e.g., the processing device 140). Therefore, the nerve fiber extraction device can determine at least one ROI of the target nerve fiber according to the obtained pre-imported configuration file and/or the received user input instruction. In some embodiments, the configuration file and input instructions may include information related to the target nerve fiber(s) that the user wants to track, such as the name or the classification of the target nerve fiber(s).

It should be noted that the above description regarding the process 900 is merely provided for the purposes of illustration, and not intended to limit the scope of the present disclosure. For persons having ordinary skills in the art, multiple variations or modifications may be made under the teachings of the present disclosure. However, those variations and modifications do not depart from the scope of the present disclosure.

Figure 10:
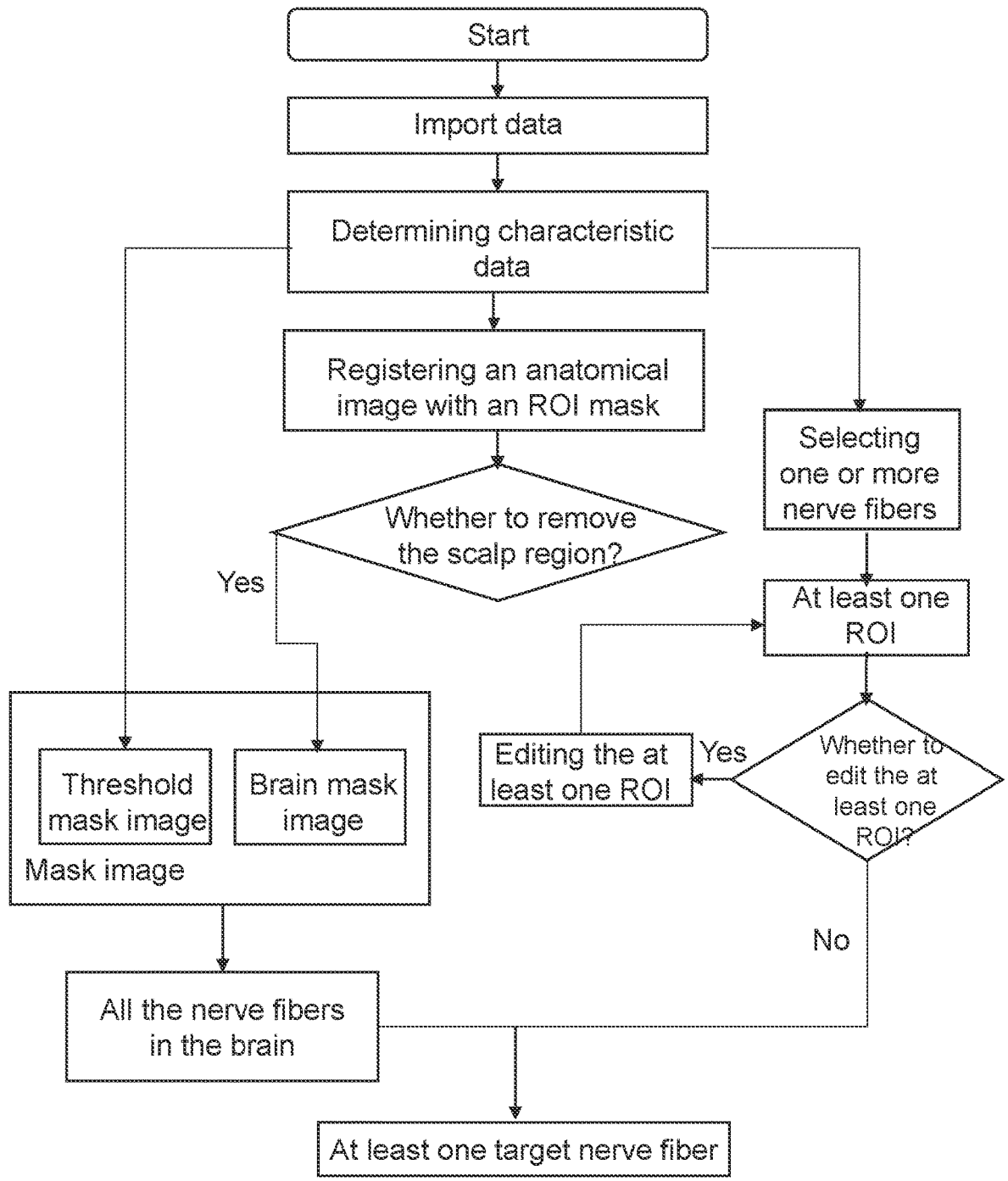
FIG. 10 is a schematic diagram illustrating an exemplary method for extracting at least one target nerve fiber according to some embodiments of the present disclosure.

FIG. 10 is a schematic diagram illustrating an exemplary method for extracting at least one target nerve fiber according to some embodiments of the present disclosure. After acquiring the anatomical data of the anatomical image and the diffusion data of the diffusion image, such data may be imported into the nerve fiber extraction device. The characteristic data may be determined based on the diffusion data, such as $\lambda 1$, $\lambda 2$, $\lambda 3$, FA, VR, and RA. In some embodiments, the processing device 140 may determine a mask image, and then proceed to track the at least one target nerve fiber in the mask image. The mask image may include, for example, a characteristic region mask image or a threshold mask image. Merely by way of example, the subject may be the head, and the mask image may be obtained by removing a scalp region in the diffusion image. Optionally, the threshold mask image is obtained by adjusting the threshold of the above characteristic data. As another example, the mask image may be obtained by segmenting the diffusion image. In some embodiments, to determine at least one ROI in the diffusion image, a predetermined ROI mask may be used. For example, the processing device 140 may register the anatomical data with the diffusion data to obtain registration information between the anatomical image and the diffusion image. The at least one ROI may be determined based on the anatomical data, the diffusion data, the predetermined ROI mask, and the registration information. Optionally, after the at least one ROI in the diffusion image is determined, a user may view the ROI information on a display of the terminal device and check whether the ROI information needs to be updated. The processing device 140 may obtain a reference user input regarding the ROI information, and determines whether to update at least a portion of one or more of the at least one ROI. If the user decides that at least a portion of the ROI information needs to be updated, the user may, for example, adjust the shape, the position, and/or the size of any one of the at least one ROI. If the user decides that none of the ROI information needs to be updated, the user may input an instruction to the terminal device to cause the processing device 140 to extract at least one target nerve fibers from the diffusion image based on the at least one ROI. More descriptions regarding the extraction of the at least one target nerve fiber may be found elsewhere in the present disclosure, for example, in FIG. 5, FIG. 11, and the descriptions thereof.

Figure 11:
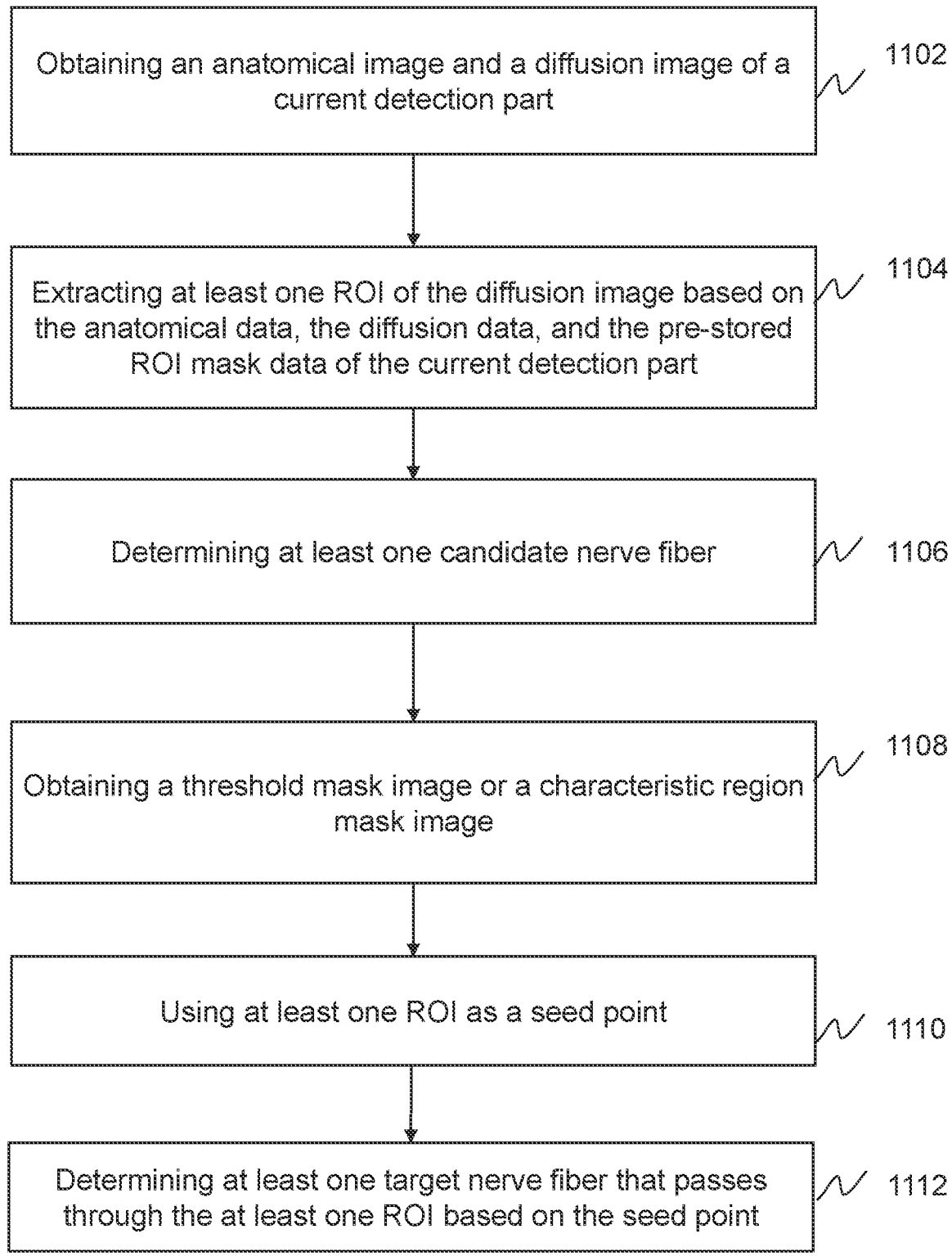
FIG. 11 is a flowchart illustrating an exemplary process for extracting at least one target nerve fiber according to some embodiments of the present disclosure.

FIG. 11 is a flowchart illustrating an exemplary process for extracting at least one target nerve fiber according to some embodiments of the present disclosure. At least a portion of process 1100 may be implemented on the nerve fiber extraction device 200 as illustrated in FIG. 2 or the nerve fiber extraction device 400 as illustrated in FIG. 4. In some embodiments, one or more operations of the process 1100 may be implemented in the system 100 as illustrated in FIG. 1. In some embodiments, one or more operations in the process 1100 may be stored in the storage device 150 and/or the storage (e.g., the storage 220, etc.) as a form of instructions, and invoked and/or executed by the system 100, or a portion thereof (e.g., the processing device 140). In some embodiments, the instructions may be transmitted in a form of electronic current or electrical signals.

In 1102, an anatomical image and a diffusion image of a current detection part may be obtained.

In 1104: at least one ROI of the diffusion image may be extracted based on the anatomical data, the diffusion data, and the pre-stored ROI mask data of the current detection part.

In 1106, at least one candidate nerve fiber may be determined. More details regarding the determination of the at least one candidate nerve fiber may be found elsewhere in the present disclosure, for example, in operation 910 and the description thereof.

In 1108, a threshold mask image or a characteristic region mask image may be obtained. In some embodiments, operation 1108 may be performed in a manner that is similar to operation 906 or 908.

In 1110, at least one ROI is used as a seed point.

In some embodiments, after obtaining the at least one ROI through the above-mentioned embodiments, the user can directly click the ROI of the diffusion image presented on a terminal device. Alternatively, the user can select one or more ROIs from a list presented on the terminal device. In some embodiments, the user may edit the at least one ROI via the terminal device. For example, the user may edit the shape of one or more ROIs. As another example, the user may remove one or more ROIs.

In 1112, at least one target nerve fiber that passes through the at least one ROI (e.g., a first ROI) may be determined based on the seed point. A tracking algorithm may be used to track the at least one target nerve fiber in the threshold mask image or the characteristic region mask. The at least one target nerve fiber may be tracked from the seed point.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure and are within the spirit and scope of the exemplary embodiments of this disclosure.

Moreover, certain terminology has been used to describe embodiments of the present disclosure. For example, the terms "one embodiment," "an embodiment," and "some embodiments" mean that a particular feature, structure, or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "module," "unit," "component," "device," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2003, Perl, COBOL 2002, PHP, ABAP, dynamic programming languages such as Python, Ruby, and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various embodiments. This method of disclosure, however, is not to be interpreted as reflecting an intention that the claimed subject matter requires more features than are expressly recited in each claim. Rather, claim subject matter lie in less than all features of a single foregoing disclosed embodiment.

What is claimed is:

1. A method for image-based nerve fiber extraction, implemented on a computing device having at least one processor and at least one non-transitory storage medium, the method comprising:
    obtaining an anatomical image of a subject and a diffusion image of the subject, the subject including at least one region of interest (ROI) that relates to extraction of at least one target nerve fiber in the subject;
    determining, based on the anatomical image, the at least one ROI in the diffusion image; and
    extracting, from the diffusion image, at least one of the at least one target nerve fiber based on the at least one ROI; wherein
        the at least one ROI includes a first ROI; the at least one target nerve fiber passes through the first ROI, and the extracting, from the diffusion image, at least one of the at least one target nerve fiber based on the at least one ROI includes:
            determining at least a portion of the first ROI as a seed point; and
            extracting, from the diffusion image and based on the seed point, the at least one of the at least one target nerve fiber that passes through the first ROI.

2. The method of claim 1, wherein the determining, based on the anatomical image, the at least one ROI in the diffusion image includes:
    determining, in the anatomical image, at least one reference region corresponding to the at least one ROI; and
    determining, based on the anatomical image and the at least one reference region, the at least one ROI in the diffusion image.

3. The method of claim 2, wherein the determining, based on the anatomical image and the at least one reference region, the at least one ROI in the diffusion image includes:
    determining registration information between the anatomical image and the diffusion image by registering the anatomical image with the diffusion image; and
    determining, in the diffusion image, the at least one ROI based on the registration information, the anatomical image, and the at least one reference region.

4. The method of claim 2, wherein the determining, in the anatomical image, at least one reference region corresponding to the at least one ROI includes:
    obtaining at least one predetermined ROI mask; and
    determining, in the anatomical image, the at least one reference region based on the at least one predetermined ROI mask.

5. The method of claim 2, wherein the determining, in the anatomical image, at least one reference region corresponding to the at least one ROI includes:
    obtaining a trained extraction model; and
    determining, in the anatomical image, the at least one reference region using the trained extraction model.

6. The method of claim 2, wherein the determining, in the anatomical image, at least one reference region corresponding to the at least one ROI includes:
    obtaining, based on at least one of a default setting or a user input, information related to the at least one target nerve fiber; and
    determining, based on the information related to the at least one target nerve fiber, the at least one reference region in the anatomical image.

7. The method of claim 1, wherein the extracting, from the diffusion image, at least one of the at least one target nerve fiber based on the at least one ROI includes:
    identifying, based on the diffusion image, at least one candidate nerve fiber using a tracking algorithm; and
    extracting, from the diffusion image, the at least one of the at least one target nerve fiber selected from the at least one candidate nerve fiber.

8. The method of claim 7, wherein the identifying, based on the diffusion image, at least one candidate nerve fiber using a tracking algorithm includes:
    determining a mask image by excluding one or more background regions from the diffusion image, the one or more background regions being unrelated to the extraction of the at least one target nerve fiber; and
    extracting, from the mask image, the at least one candidate nerve fiber using the tracking algorithm.

9. The method of claim 8, wherein the determining a mask image includes:
    determining characteristic data based on the diffusion image; and
    determining the mask image based on the characteristic data.

10. The method of claim 1, wherein the at least one ROI further includes a second ROI, wherein
    the at least one target nerve fiber does not pass through the second ROI.

11. The method of claim 1, wherein the at least one ROI further includes a second ROI, and the extracting, from the diffusion image and based on the diffusion image, the at least one of the at least one target nerve fiber that passes through the first ROI includes:
  determining, in the diffusion image and based on the seed point, at least one candidate nerve fiber that passes through the first ROI using a tracking algorithm; and
  for each of the at least one candidate nerve fiber,
  determining whether the candidate nerve fiber passes through the second ROI; and
  in response to determining that the candidate nerve fiber does not pass through the second ROI, designating the candidate nerve fiber as one of the at least one target nerve fiber.

12. A system, comprising:
  at least one non-transitory storage medium including a set of instructions for image-based nerve fiber extraction; and
  at least one processor in communication with the at least one non-transitory storage medium, wherein when executing the set of instructions, the at least one processor is configured to cause the system to perform operations including:
  obtaining an anatomical image of a subject and a diffusion image of the subject, the subject including at least one region of interest (ROI) that relates to extraction of at least one target nerve fiber in the subject;
  determining, based on the anatomical image, the at least one ROI in the diffusion image; and
  extracting, from the diffusion image, at least one of the at least one target nerve fiber based on the at least one ROI; wherein
    the at least one ROI includes a first ROI; the at least one target nerve fiber passes through the first ROI, and the extracting, from the diffusion image, at least one of the at least one target nerve fiber based on the at least one ROI includes:
      determining at least a portion of the first ROI as a seed point; and
      extracting, from the diffusion image and based on the seed point, the at least one of the at least one target nerve fiber that passes through the first ROI.

13. The system of claim 12, wherein the determining, based on the anatomical image, the at least one ROI in the diffusion image includes:
  determining, in the anatomical image, at least one reference region corresponding to the at least one ROI; and
  determining, based on the anatomical image and the at least one reference region, the at least one ROI in the diffusion image.

14. The system of claim 13, wherein the determining, based on the anatomical image and the at least one reference region, the at least one ROI in the diffusion image includes:
  determining registration information between the anatomical image and the diffusion image by registering the anatomical image with the diffusion image; and
  determining, in the diffusion image, the at least one ROI based on the registration information, the anatomical image, and the at least one reference region.

15. The system of claim 13, wherein the determining, in the anatomical image, at least one reference region corresponding to the at least one ROI includes:
  obtaining at least one predetermined ROI mask; and
  determining, in the anatomical image, the at least one reference region based on the at least one predetermined ROI mask.

16. The system of claim 13, wherein the determining, in the anatomical image, at least one reference region corresponding to the at least one ROI includes:
  obtaining a trained extraction model; and
  determining, in the anatomical image, the at least one reference region using the trained extraction model.

17. The system of claim 12, wherein the extracting, from the diffusion image, at least one of the at least one target nerve fiber based on the at least one ROI includes:
  identifying, based on the diffusion image, at least one candidate nerve fiber using a tracking algorithm; and
  extracting, from the diffusion image, the at least one of the at least one target nerve fiber selected from the at least one candidate nerve fiber.

18. The system of claim 17, wherein the identifying, based on the diffusion image, at least one candidate nerve fiber using a tracking algorithm includes:
  determining a mask image by excluding one or more background regions from the diffusion image, the one or more background regions being unrelated to the extraction of the at least one target nerve fiber; and
  extracting, from the mask image, the at least one candidate nerve fiber using the tracking algorithm.

19. A non-transitory computer readable medium, comprising at least one set of instructions, wherein when executed by at least one processor of a computing device, the at least one set of instructions direct the at least one processor to perform operations including:
  obtaining an anatomical image of a subject and a diffusion image of the subject, the subject including at least one region of interest (ROI) that relates to extraction of at least one target nerve fiber in the subject;
  determining, based on the anatomical image, the at least one ROI in the diffusion image; and
  extracting, from the diffusion image, at least one of the at least one target nerve fiber based on the at least one ROI; wherein
    the at least one ROI includes a first ROI; the at least one target nerve fiber passes through the first ROI, and the extracting, from the diffusion image, at least one of the at least one target nerve fiber based on the at least one ROI includes:
      determining at least a portion of the first ROI as a seed point; and
      extracting, from the diffusion image and based on the seed point, the at least one of the at least one target nerve fiber that passes through the first ROI.

* * * * *